United States Patent [19]

Himmele et al.

[11] Patent Number: 4,656,282

[45] Date of Patent: Apr. 7, 1987

[54] PREPARATION OF SUBSTITUTED PIPERIDINES

[75] Inventors: Walter Himmele, Walldorf; Walter-Wielant Wiersdorff, Mutterstadt; Marco Thyes, Ludwigshafen, all of Fed. Rep. of Germany

[73] Assignee: BASF Aktiengesellschaft, Ludwigshafen, Fed. Rep. of Germany

[21] Appl. No.: 794,744

[22] Filed: Nov. 4, 1985

[30] Foreign Application Priority Data

Nov. 16, 1984 [DE] Fed. Rep. of Germany ....... 3441929

[51] Int. Cl.⁴ .................. C07D 211/12; C07D 211/14; C07D 217/02; C07D 217/04
[52] U.S. Cl. .................................... 546/150; 546/112; 546/184; 546/192; 546/203; 546/205
[58] Field of Search ............... 546/184, 192, 150, 151, 546/112, 203, 205

[56] References Cited

PUBLICATIONS

Borch et al., "J. American Chem. Soc.", vol. 93, pp. 2897-2904 (1971).
Kirk-Othmer "Encyclopedia of Chemical Technology", vol. 7, pp. 692, 693 and 697 (1951).
Gilman's Organic Chemistry, vol. 1, 2nd Edition, Chapter 9, pp. 779-833 (1943), fifth printing Jun. 1947.
Houben-Weyl, vol. 11/1, (1957), pp. 693-695, 698,278, 593/594, 117 and 225.
Org. Synth. Coll. vol. IV (1963), pp. 795 and 816.
Nielsen, J. Heterocycl. Chem. 12 (1975) pp. 1, 161.
Y. Watanabe et al., Bull. Chem. Soc. Jap. 49 (1976) 8, 2302.
C. F. Lane, *Synthesis* (1975), 135-142.

*Primary Examiner*—John M. Ford
*Attorney, Agent, or Firm*—John H. Shurtleff

[57] ABSTRACT

Piperidines substituted in the 3- and/or 4-position are prepared by reacting a glutardialdehyde substituted in the 2- and/or 3-position with ammonia or a primary amine and hydrogen at elevated temperature and under superatmospheric pressure in the presence of a hydrogenation catalyst.

15 Claims, No Drawings

PREPARATION OF SUBSTITUTED PIPERIDINES

The present invention relates to a process for the preparation of piperidines which are substituted in the 3- and/or 4-position and may furthermore be alkylated at the nitrogen.

Piperidines are very important in the synthesis of active ingredients. Piperidines carrying different substituents are required both for active compounds for drugs and for active ingredients used in crop protection.

They are prepared, as a rule, by reducing substituted pyridines, pyridinium salts or cyclic amides (Houben-Weyl, vol. 11/1, 1957, pages 693–695, 698, 728 and 593/594). For synthesis from acyclic educts, for example, substituted 1,5-dihalides, 1,5-haloamines, 1,5-diamino alcohols, 1,5-diamines or N-arylglutarimides are used as starting materials. (Houben-Weyl, vol. 11/1, 1957, pages 117 and 255, and Org. Synth. Coll. vol. IV, 1963, pages 795 and 816).

There are only a few examples of the synthesis of piperidines by reductive amination of glutardialdehyde. For example, J. Heterocycl. Chem. 12 (1975) 1, 161 describes the reaction of 7-amino-1,3,5-triazaadamantane with glutardialdehyde and hydrogen in the presence of a platinum oxide catalyst. N-substituted piperidines can be prepared from glutardialdehyde and primary amines, using tetracarbonyl hydridoferrate (Y. Watanabe et al., Bull. Chem. Soc. Jap. 49 (1976) 8, 2302). C. F. Lane recommends the use of sodium cyanoborohydride as a selective reducing agent for converting, for example, 1,4- or 1,5-dicarbonyl compounds with primary amines or ammonia to 5-membered or 6-membered heterocycles (Synthesis 1975, 135). To date, C-substituted piperidines have not been synthesized by reductive amination of a glutardialdehyde derivative.

Despite the variety of methods of synthesis, it is difficult to obtain certain substitution patterns.

It is an object of the present invention to provide a simple means for obtaining substituted piperidines, in particular those which are substituted in the 3- and 4-position and may furthermore be substituted at the nitrogen.

We have found that this object is achieved, and that piperidines substituted in the 3- and/or 4-position and of the general formula (I)

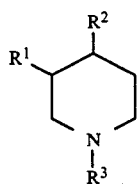

where $R^1$ and $R^2$ are identical or different and are each straight-chain or branched alkyl, cycloalkyl, aryl or aralkyl, or are bonded to one another to form a 5-membered or 6-membered ring, or one of the radicals $R^1$ or $R^2$ is hydrogen, and $R^3$ is $C^1$–$C^4$-alkyl or hydrogen, can be prepared in a particularly advantageous manner if a glutardialdehyde substituted in the 2- and/or 3-position and of the general formula (II)

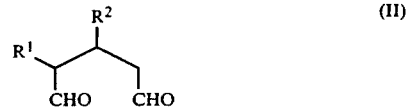

where $R^1$ and $R^2$ have the above meanings, is reacted with ammonia or a primary amine of 1 to 4 carbon atoms and hydrogen at elevated temperatures and under superatmospheric pressure in the presence of a hydrogenation catalyst to give a piperidine derivative (I).

The hydrogenation of glutardialdehydes substituted in the 2- and/or 3-position under aminating conditions, which takes place in accordance with the equation below, gives piperidines substituted in the 3- and/or 4-position in good yield and with good selectivity:

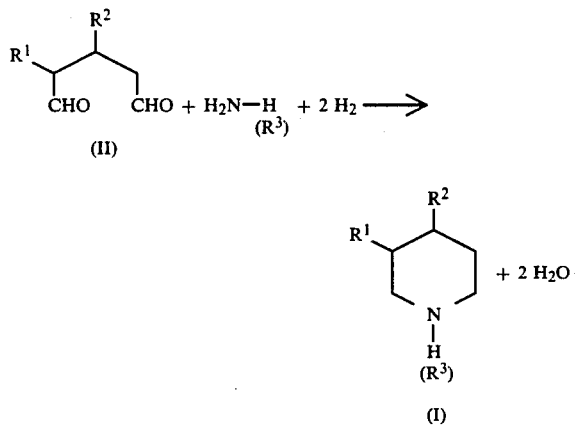

The glutardialdehydes (II) are advantageously prepared by acidic hydrolysis of a 2-alkoxy-3,4-dihydropyran substituted in the 4- and/or 5-position, for example as described in German Laid-Open Application DOS No. 968,511. Since they are not very stable in pure form, they are used in the form of solvent/glutardialdehyde mixtures. The solvent component which is added to the dial (II) in order to stabilize it should possess solubility characteristics such that the second liquid phase is not formed during the reaction. Solvents which are useful both for stabilizing the dialdehyde and for the hydrogenation of the dial/solvent mixture under aminating conditions are dioxane and low molecular weight dialkyl ethers of a glycol, eg. ethylene glycol dimethyl ether or ethylene glycol diethyl ether. Tetrahydrofuran is particularly useful.

In many cases, it is possible for the crude reaction mixture obtained after cleavage of the 6-alkoxy dihydropyran, and after heating has been carried out and the free formic acid distilled off, to be used directly for the hydrogenation under aminating conditions, thus saving one operation, ie. the purification of the dial (II) by distillation, and hence avoiding losses of substance.

Glutardialdehydes (II) suitable for the novel process are those in which the radicals $R^1$ and/or $R^2$ are straight-chain or branched alkyl, for example of 1 to 20, in particular 1 to 10, advantageously 1 to 5, carbon atoms, eg. methyl, ethyl, propyl, isopropyl, butyl, isobutyl, tert.-butyl, pentyl or isopropyl. The alkyl radicals may be further substituted by groups which are inert under the reaction conditions, eg. alkoxy of 1 to 4 carbon atoms.

Other suitable radicals $R^1$ and/or $R^2$ are cycloalkyl radicals of 5 to 8 carbon atoms. $R^1$ and $R^2$ may furthermore be bonded to one another to form a 5-membered or 6-membered ring.

The radicals $R^1$ and/or $R^2$ may furthermore be aryl of 6 to 15 carbon atoms or aralkyl of 7 to 16 carbon atoms. In addition to alkyl substituents, such as methyl, ethyl, propyl, isopropyl, butyl, isobutyl, tert.-butyl, pentyl and isopentyl, the aromatic nuclei may be further substituted by groups which are inert under the reaction conditions, eg. alkoxy or halogen.

$R^1$ and $R^2$ may be identical or different, and one of the two radicals $R^1$ or $R^2$ may furthermore be hydrogen.

Suitable amine components are low molecular weight alkylamines of 1 to 4 carbon atoms, eg. butyl-, propyl- and ethylamine. Particularly suitable amines are those which are gaseous at room temperature, eg. methylamine and especially ammonia. The amine component is advantageously used in an excess with respect to (II). As a rule, from 1.1 to 7.0, in particular from 1.5 to 4, moles of amine or ammonia are used per mole of glutardialdehyde (II).

In order to avoid the formation of two liquid phases in the autoclave during the hydrogenation under aminating conditions, it is advantageous to mix the amine or ammonia with a low molecular weight alcohol, eg. methanol, ethanol or isopropanol. Higher alcohols which form two-phase mixtures even with anhydrous ammonia are not very suitable.

The hydrogenation of (II) under aminating conditions is carried out at, for example, from 50° to 200° C., in particular from 70° to 120° C., advantageously from 80° to 110° C., in the presence of a suitable hydrogenation catalyst under superatmospheric pressure by a conventional method.

The hydrogenation catalysts are prepared using, for example, the platinum metals ruthenium, rhodium, palladium, iridium and platinum, and nickel and cobalt. The catalysts used can be without a carrier, eg. Raney nickel or Raney cobalt, or may be in the form of supported catalysts. The unsupported catalysts may furthermore be compounds of the metals according to the invention, preferably their oxides. Examples of suitable carriers are carbon, silica gel, aluminum silicate and alumina. Such supported catalysts can be prepared by any method, for example by impregnating the carrier with appropriate solutions of the metal salts, by kneading or mixing of the components, accompanied by milling. Regarding details of the preparation of catalysts, in particular supported catalysts, reference may be made to Houben-Weyl, Methoden der Organischen Chemie, volume 4/2, page 137 et seq. In supported catalysts, the metal content of the catalyst is usually from 0.05 to 19.5, preferably from 0.5 to 15, % by weight, based on the weight of the carrier. The metal of the hydrogenation catalysts is used, as a rule, in an amount of from 0.1 to 100, in particular from 0.5 to 20, % by weight, based on starting material II.

Raney cobalt and Raney nickel have proven particularly useful hydrogenation catalysts. When the reaction is complete, the catalyst can be separated from the reaction mixture by filtration or sedimentation and is advantageously used for a further hydrogenation.

The hydrogen pressure can be varied within wide limits. In order to achieve an optimum yield, selection of the pressure depends on the intensity with which the reaction mixture is stirred. Since the reaction takes place in the liquid phase, the provision of hydrogen for the hydrogenation reaction at the suspended catalyst must be optimally set both by means of the solubility and by means of the continued feed for the reaction. Under low hydrogen partial pressures, vigorous stirring may be employed; on the other hand, it has proven advantageous to permit the reaction to take place under a fairly high hydrogen partial pressure when the contents of the autoclave are mixed with an anchor stirrer providing less vigorous stirring.

Particularly useful for the novel process are autoclaves which are equipped with magnetic lift stirrers. The catalyst in alcohol is initially taken in such an autoclave, the amine component is injected and then mixture is heated to the reaction temperature, after which the total pressure is brought to 100–300, in particular 100–200, preferably 130–170, bar by subsequently forcing in hydrogen.

In an advantageous procedure, the reaction conditions, such as pressure and temperature, are first established and the glutardialdehyde/solvent mixture is then introduced uniformly over a period of several hours, as a rule from 5 to 10, in particular from 6 to 8, hours, advantageously with thorough gassing and stirring. When the stabilized glutardialdehyde has been injected into the autoclave, the reaction mixture is advantageously stirred for several hours longer, as a rule from 2 to 6 hours, under the reaction conditions.

Working up is advantageously carried out by, for example, cooling the reaction mixture, and the excess ammonia or the amine and the hydrogen are expelled in gaseous form during the cooling phase in order to accelerate cooling. The catalyst is separated off, after which the alcohol and the dial solvent, and the water produced during the reaction, are distilled off. Both the solvent and the amine component can be reused for further reactions.

The piperidines prepared by the novel process can be isolated from the remaining reaction mixture by fractional distillation by a conventional method, under atmospheric pressure or, particularly in the case of bulky substituents, under reduced pressure.

The novel hydrogenation of (II) under aminating conditions gives the substituted piperidines in good yield and high purity. In the synthesis of the products substituted in the 3- and 4-position, the transconfiguration of the radicals $R^1$ and $R^2$ predominates.

The Examples which follow illustrate the invention. Example 12 illustrates the preparation of fungicidal compounds from the piperidines substituted in the 3- and/or 4-position, by alkylation at the nitrogen. Substituted, in particular aryl-substituted, piperidines also serve as building blocks for the synthesis of compounds possessing useful pharmacological properties, eg. platelet aggregation-inhibiting properties. Thus, using the process described on pages 7 to 9 of German Laid-Open Application DOS No. 3,302,021 (O.Z.: 36350), it is possible to obtain, for example, 6-aryl-4,5-dihydro-3-(2H)-pyridazinones of the formula

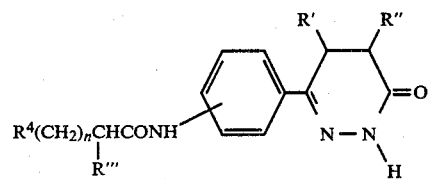

where $R^4$ is piperidyl which is substituted in the 3- and/or 4-position, by reacting the corresponding halo compound with a piperidine which is unsubstituted at the nitrogen, in the presence or absence of a base and/or of an iodide as a catalyst.

EXAMPLE 1

Synthesis of 4-phenylpiperidine by hydrogenating distilled 3-phenylglutardialdehyde under aminating conditions.

100 g of Raney cobalt in 625 g of methanol are introduced into a 5 l autoclave equipped with a magnetic lift stirrer. The autoclave is closed so that it is pressure-tight, and is flushed with nitrogen. After 500 g of ammonia have been injected, the autoclave is heated to 110° C., and the total pressure is brought to 150 bar by forcing in hydrogen. The stirrer is switched on. 200 g/h of a mixture of 938 g of about 99% pure distilled 3-phenylglutardialdehyde and 469 g of tetrahydrofuran are pumped into the autoclave in the course of 7 hours. After the dialdehyde mixture has been pumped in, the injection line is flushed free by pumping in 200 g of tetrahydrofuran. After this glutardialdehyde solution has been injected, the autoclave is kept under the stated reaction conditions for a further 6 hours. Hydrogen consumed is replaced hourly in order to maintain the desired hydrogen partial pressure.

When the reaction is complete, the mixture is cooled to 60° C. and the hydrogen and some of the excess ammonia are let down.

When the gas still present in the autoclave has been let down, the autoclave is flushed with nitrogen and its contents are removed and separated off from the suspended Raney cobalt by filtration.

In a short path distillation apparatus, ammonia, tetrahydrofuran and methanol are first stripped off under 67 mbar, after which the water formed during the reaction is distilled over by heating and reducing the pressure to 40 mbar. The 4-phenylpiperidine formed passes over at from 146° to 156° C. under the same pressure, 654 g of this product being obtained. According to gas chromatographic analysis, this fraction consists of 4-phenylpiperidine having a purity greater than 99.5%. The amine crystallizes to form long needles. The melting point is 63° C. and the yield is 59.6%, based on the 3-phenylglutardialdehyde used. The quality obtained meets the requirements in respect of further processing for the synthesis of active ingredients.

EXAMPLE 2

Synthesis of 4-phenylpiperidine by hydrogenation of undistilled 3-phenylglutardialdehyde under aminating conditions 1,165 g of 3-phenylglutardialdehyde, obtained by acidolysis of 1,560 g of 4-phenyl-6-isobutoxy-5,6-dihydropyran, are freed from solvent and formic acid by incipient distillation, mixed with 291 g of tetrahydrofuran for stabilization, and converted to 4-phenylpiperidine as described under Example 1.

When the reaction mixture (2,627 g) is worked up by filtration, removal of the solvent and subsequent fractionation of the 4-phenylpiperidine, 736 g of 4-phenylpiperidine having a purity greater than 99.5% are obtained under 40 mbar and at from 146° to 164° C. 81 g of tailings obtained in the distillation contain a further 57 g of amine, although only about 70% of 4-phenylpiperidine are present in these tailings.

The yield of amine which can be utilized directly for syntheses of active ingredients is 68.1%, based on the 4-phenyl-6-isobutoxy-5,6-dihydropyran introduced into the reaction. If the amount of amine present in the tailings is taken into account, the resulting yield is 73.2%.

Examples 3 to 11, which are carried out similarly to Example 1, are summarized in Table 1.

TABLE 1

Synthesis of piperidines substituted in the 3- and 4-position, by hydrogenation of subsituted glutardialdehydes under aminating conditions

| Example number | $R^1$ | $R^2$ | $R^3$ | °C./mbar | Yield of substituted piperidine in % | Cis/trans ratio of the substituents $R^1$ and $R^2$ |
|---|---|---|---|---|---|---|
| 3 | $CH_3$ | $C_2H_5$ | H | 106/200 | 82 | |
| 4 | $C_2H_5$ | $n$-$C_3H_7$ | H | 99/32 | 88 | |
| 5 | $n$-$C_3H_7$ | $n$-$C_4H_9$ | H | 123/27 | 91 | |
| 6 | $i$-$C_3H_7$ | $i$-$C_4H_9$ | H | 125/37 | 87 | |
| 7 | —$CH_3$ | —C$_6$H$_5$ | H | 140/20 | 73 | 15:85 |
| 8 | $CH_3$ | —C$_6$H$_4$-tBu | H | 156/2.7 | 75 | 17:83 |
| 9 | $C_2H_5$ | $n$-$C_3H_7$ | —$CH_3$ | 129/146 | 58 | |
| 10 | H | —C$_6$H$_5$ | —$CH_3$ | 130/29 | 72 | |
| 11 | $CH_3$ | —C$_6$H$_4$-tBu | —$CH_3$ | 118/0.3 | 60 | 35:65 |

EXAMPLE 12

Alkylation of 4-(4'-tert.-butylphenyl)-3-methylpiperidine. Synthesis of N-hexahydrobenzyl-4-(4'-tert.-butylphenyl)-3-methylpiperidine (X)

30 g of 4-(4'-tert.-butylphenyl)-3-methylpiperidine (from Example 8) are mixed with 17.5 g of hexahydrobenzaldehyde, the mixture is left to stand for two hours and 36 g of formic acid are then added. This reaction mixture is refluxed for 12 hours.

Fractionation by a short path distillation gives the following fractions:

| | | |
|---|---|---|
| 1. up to 185° C./7 mbar: | 4 g | about 86% of (X) |
| 2. up to 190° C./7 mbar: | 31 g | according to gas chromatographic analysis |
| Distillation residue | 4 g | |

The NMR and IR spectra confirm the presence of the compound (X), which, according to Application No. P 31 41 927.6 (O.Z. 0050/37447), can be used as a fungicide. The N-formyl product of the educt is still present as an impurity.

We claim:

1. A process for the preparation of a piperidine which is substituted in the 3- and 4-position and is of the formula

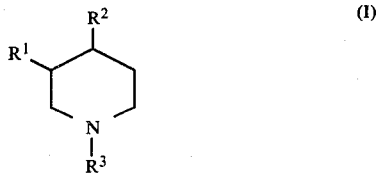

where $R^1$ and $R^2$ are identical or different and are each straight-chain or branched alkyl, cycloalkyl, aryl or aralkyl, or may be bonded to one another to form a 5-membered or 6-membered ring, or one of the radicals $R^1$ or $R^2$ may be hydrogen, and $R^3$ is $C_1-C_4$-alkyl or hydrogen, which process comprises:

reacting (a) a glutardialdehyde which is substituted in the 2- and/or 3-position and is of the formula

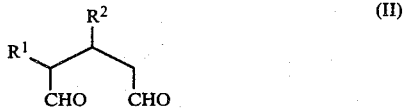

where $R^1$ and $R^2$ have the above meanings, is reacted with (b) ammonia or a primary amine of 1 to 4 carbon atoms and (c) hydrogen, at elevated temperatures and under superatmospheric pressure and in the presence of a hydrogenation catalyst selected from the group consisting of the metals nickel and cobalt and compounds of said metals.

2. A process as claimed in claim 1, wherein the reaction is carried out at from 70° to 140° C.

3. A process as claimed in claim 1, wherein Raney cobalt or Raney nickel is used as the hydrogenation catalyst.

4. A process as claimed in claim 1, wherein ammonia or methylamine is used as the amine component.

5. A process as claimed in claim 4, wherein from 1.1 to 7.0 moles of the amine component are used per mole of substituted glutardialdehyde (II).

6. A process as claimed in claim 1, wherein the amine component is dissolved in a low molecular weight alcohol before being reacted with (II).

7. A process as claimed in claim 6, wherein methanol, ethanol or isopropanol is used as the low molecular weight alcohol.

8. A process as claimed in claim 1, wherein the reaction is carried out under a total pressure of from 50 to 300 bar.

9. A process as claimed in claim 1, wherein the substituted glutardialdehyde (II) is used as a mixture with an inert solvent.

10. A process as claimed in claim 9, wherein tetrahydrofuran, dioxane or a low molecular weight dialkyl ether of a glycol is used as a diluent for the glutardialdehyde.

11. A process as claimed in claim 1, wherein the catalyst is separated off after the reaction, and the piperidine derivative (I) is isolated from the crude reaction mixture by fractional distillation.

12. A process as claimed in claim 1, wherein the reaction is carried out at a temperature of from 80° to 110° C.

13. A process as claimed in claim 4, wherein from 1.5 to 4.0 moles of the amine component are used per mole of substituted glutardialdehyde (II).

14. A process as claimed in claim 1, wherein the reaction is carried out under a total pressure of from 100 to 200 bar.

15. A process as claimed in claim 1, wherein the reaction is carried out under a total pressure of from 130 to 170 bar.

* * * * *